US00PP19128P2

(12) United States Plant Patent
Zary

(10) Patent No.: US PP19,128 P2
(45) Date of Patent: Aug. 19, 2008

(54) FLORIBUNDA ROSE PLANT NAMED 'JACOUTRA'

(50) Latin Name: *Rosa hybrida*
Varietal Denomination: JACoutra

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 11/824,486

(22) Filed: Jun. 29, 2007

(51) Int. Cl.
*A01H 5/00* (2006.01)

(52) U.S. Cl. ..... Plt./146
(58) Field of Classification Search ..... Plt./146
See application file for complete search history.

(56) References Cited

U.S. PATENT DOCUMENTS

PP4,297 P * 9/1978 McGredy, IV ..... Plt./150
PP12,073 P2 * 8/2001 Zary ..... Plt./141

* cited by examiner

*Primary Examiner*—Wendy C. Haas
(74) *Attorney, Agent, or Firm*—Klarquist Sparkman, LLP

(57) ABSTRACT

Floribunda rose plant having very large flowers in small clusters, a very compact, well-branched plant habit; glossy, dark green foliage, distinctive fruity fragrance and excellent resistance to rust and powdery mildew.

1 Drawing Sheet

Genus and species: *Rosa hybrida.*
Variety denomination: 'JACoutra'.

ORIGIN OF THE INVENTION

The present invention relates to a new and distinct variety of a floribunda rose plant named 'JACoutra' which was originated by me by crossing the variety 'JACimpac' (female parent, not patented), with the variety 'JACzap' (male parent, Plant Pat. No. 12,073).

BACKGROUND OF THE INVENTION

The primary objective of this breeding was to produce a new floribunda rose variety having the compact free flowering qualities of the female (seed) parent combined with the large flowers of the male (pollen) parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Very large flowers in small clusters.
2. Very compact, well-branched plant habit.
3. Glossy, dark green foliage.
4. Excellent resistance to rust and powdery mildew.
5. Distinctive fruity fragrance.

Asexual reproduction of this new variety by cuttings, as performed at Wasco, Calif., shows that the foregoing characteristics and distinctions come true to form and are established and transmitted through succeeding propagations.

COMPARISON WITH PARENTS

'JACimpac' differs in flower color (light apricot for 'JACimpac' versus orange for 'JACoutra'). 'JACzap' differs in flower color from 'JACoutra' (coral orange with yellow reverse for 'JACzap' versus orange for 'JACoutra').

COMPARISON WITH SIMILAR VARIETY

The closest variety is believed to be 'MACtrum' (Plant Pat. No. 4,297). 'JACoutra' has much larger flowers (less than 4 inches for 'MACtrum' and as large as 5 inches for 'JACoutra'.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:
*Seed parent.*—'JACimpac' (not patented).
*Pollen parent.*—'JACzap' (Plant Pat. No. 12,073).

FLOWER

Observations made from January 2006 to June 2007 from plants commencing at two to three years of age grown in a garden environment at Somis, Calif.

Blooming habit: Continuous.

Bud:

*Size.*—About 40 mm long and 25 mm in diameter when the petals start to unfurl.

*Form.*—The bud form is long, pointed ovoid to globular.

*Color.*—When sepals first divide, bud color is Red Group 43B. When half blown, the upper sides of the petals are Red Group 43C and the lower sides of the petals are Red Group 43C.

*Sepals*—Color: Upper surface: Green Group 138B. Lower surface: Yellow-Green Group 146C often overlain with Red-Purple Group 183A where exposed to direct sun. Length: 28–30 mm. Width: 9–11 mm. Shape: Subulate. Surface texture: Hoary. There are three normally appendaged sepals. There are two unappendaged sepals with hairy edges.

*Receptacle.*—Color: Yellow-Green Group 146B. Shape: Funnel. Size: Medium, about 10 mm long×12 mm in diameter. Surface: Smooth.

*Peduncle.*—Length: Short, averaging about 45–50 mm. Surface: Rough, with prickles. Color: Yellow-Green Group 146B, overlain in bright sunshine with Red-Purple Group 183A. Strength: Stiff, erect.

Bloom:

*Size.*—Large. Average open diameter is about 12–13 cm.

*Borne.*—Singly and several together clusters of 3–5 blooms having pyramidal shape.

*Stems.*—Strength. Strong. Average length is about 30–35 cm with a diameter of 7–9 mm.

*Form.*—When first open: High centered. Permanence: Flattens, outer petals curl back.

*Petalage.*—Number of petals under normal conditions: 25. Color: The upper sides of the petals are Red Group 43C. The reverse sides of the petals are Red Group 43C. The base of the petals has an approximately 5 mm×5 mm Yellow Group 6A color spot. The major color on the upper sides is Red Group 43C.

*Discoloration.*—The general tonality at the end of the first day: No change. At the end of the third day: No change. Further aging: Day 4–5, there is some discoloration to Red Group 45D.

*Fragrance.*—Moderate. Fruity.

Petals:

*Texture.*—Thick.

*Surface.*—Smooth.

*Shape.*—Round to obovate.

*Margin.*—Entire.

*Apex shape.*—Rounded.

*Base shape.*—Rounded.

*Form.*—Flat, tips slightly recurved.

*Arrangement.*—Imbricated.

*Petaloids.*—Number: 1–3. Size: 3–7 mm long, 3–5 mm wide. Color: Red Group 43C.

*Persistence.*—Petals drop off cleanly before drying.

*Lastingness.*—On the plant: Fair (about 5 days). As a cut flower: Fair (about 7 days).

Reproductive parts:

*Stamens.*—Number: 50–70. Length: 10–12 mm. Anthers: Length: 3–5 mm. Color: Yellow-Orange Group 23D. Arrangement: Regular around styles. Filaments: Color: Bottom one-third: Yellow Group 12C. Top two-thirds: Red Group 41A. Length: 5–9 mm. Pollen: Color: Orange Group 26A.

*Pistils.*—Number: 40–50 Length: 5–8 mm. Styles: Color: Red Group 45B. Length: 4–7 mm. Stigmas: Color: Greyed-Orange Group 165D. Length: 1 mm.

*Hips.*—None observed.

PLANT

*Form.*—Bush.

*Growth.*—Medium vigor, upright, branching, compact.

*Age to maturity.*—Two years.

*Mature plant.*—Height: 3 ft. Width: 3 ft.

Foliage: Number of leaflets on normal mid-stem leaves: 3–7.

*Size.*—Large. About 11–14 cm long, 10–13 cm wide.

*Quantity.*—Normal.

*Color.*—New foliage: Upper side: Blend of Greyed-Red Group 178A and Yellow-Green Group 146A. Lower side: Greyed-Red Group 181A. Old foliage: Upper side: Green Group 136B. Lower side: Green Group 143B.

Leaflets:

*Size.*—About 4–9 cm long and 2–5 cm wide.

*Shape.*—Pointed oval.

*Base shape.*—Oblique.

*Apex shape.*—Cuspidate.

*Texture.*—Leathery.

*Edge.*—Serrated.

*Serrations.*—Single, small.

*Petiole.*—Color: Yellow-Green Group 144B.

*Petiole rachis.*—Color: Yellow-Green Group 144B.

*Auricles.*—Subulate.

*Stipules.*—Length: 10–15 mm, bearded.

*Disease resistance.*—Resistant to mildew and rust, susceptible to blackspot under normal growing conditions.

*Pest resistance.*—Not observed.

*Vein color.*—Yellow-Green Group 144B.

*Venation pattern.*—Reticulate.

Wood:

*New wood.*—Color: Greyed-Red Group 178A. Bark: Smooth, glandular.

*Old wood.*—Color: Green Group 143B. Bark: Smooth.

Prickles:

*Quantity.*—Many, on main canes from base: 20–25 per 150 mm of cane. Many, on laterals from main canes: 20–25 per 150 mm of cane.

*Form.*—Straight.

*Length.*—10–14 mm.

*Color when young.*—Greyed-Yellow Group 160D at base with Red Group 43C at apex.

*Color when mature.*—Greyed-Yellow Group 160D.

Small prickles:

*Quantity.*—On main stalks: Many. On laterals: Many.

*Color.*—Mostly Red Group 43C with touch of Greyed-Yellow Group 160D.

Winter hardiness: Hardy to Zone 5.

I claim:

1. A new and distinct variety of floribunda rose plant, substantially as herein shown and described, characterized particularly by its very large flowers in small clusters, very compact, well-branched plant habit with glossy, dark green foliage, distinctive fruity fragrance and excellent resistance to rust and powdery mildew.

* * * * *

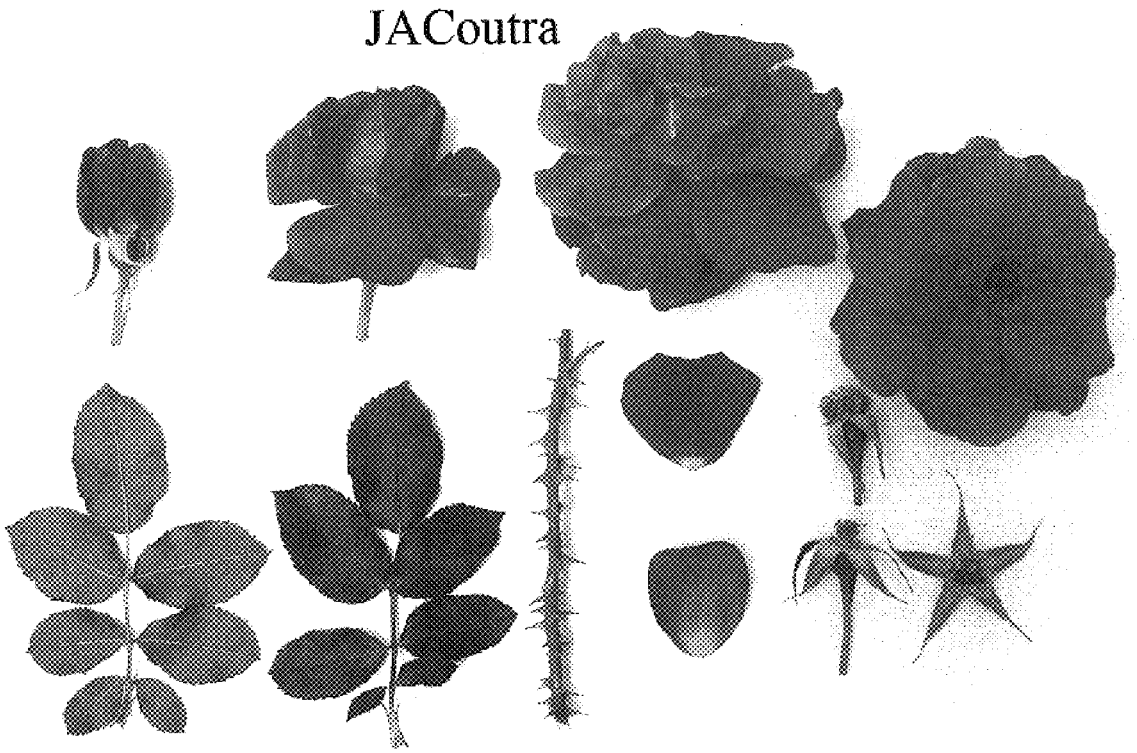
JACoutra

UNITED STATES PATENT AND TRADEMARK OFFICE

CERTIFICATE OF CORRECTION

PATENT NO. : PP 19,128 P2
APPLICATION NO. : 11/824486
DATED : August 19, 2008
INVENTOR(S) : Keith W. Zary It is certified that error appears in the above-identified patent and that said Letters Patent is hereby corrected as shown below:

In the Specification:

Column 4, line 19, "Greyed-Red Group 181A." should read --Greyed-Red Group 181B.--

Signed and Sealed this

Ninth Day of June, 2009

JOHN DOLL
*Acting Director of the United States Patent and Trademark Office*